(12) United States Patent
Rayner

(10) Patent No.: US 10,799,586 B2
(45) Date of Patent: Oct. 13, 2020

(54) HYPERTHERMIC CANCEROUS TISSUE ABLATION

(71) Applicant: Gary Rayner, Henderson, NV (US)

(72) Inventor: Gary Rayner, Henderson, NV (US)

( * ) Notice: Subject to any disclaimer, the term of this patent is extended or adjusted under 35 U.S.C. 154(b) by 410 days.

(21) Appl. No.: 15/589,904

(22) Filed: May 8, 2017

(65) Prior Publication Data

US 2017/0319257 A1     Nov. 9, 2017

Related U.S. Application Data

(60) Provisional application No. 62/332,773, filed on May 6, 2016.

(51) Int. Cl.

| | |
|---|---|
| *A61B 18/08* | (2006.01) |
| *A61B 18/10* | (2006.01) |
| *A61B 5/01* | (2006.01) |
| *A61K 41/00* | (2020.01) |
| *A61B 18/04* | (2006.01) |
| *A61B 5/00* | (2006.01) |
| *A61F 7/00* | (2006.01) |
| *A61B 18/00* | (2006.01) |

(52) U.S. Cl.
CPC ........ *A61K 41/0052* (2013.01); *A61B 5/0071* (2013.01); *A61B 5/0082* (2013.01); *A61B 5/01* (2013.01); *A61B 5/015* (2013.01); *A61F 7/0053* (2013.01); *A61B 2018/00577* (2013.01); *A61B 2018/00714* (2013.01); *A61B 2018/00791* (2013.01); *A61B 2018/046* (2013.01); *A61F 2007/009* (2013.01); *A61F 2007/0054* (2013.01)

(58) Field of Classification Search
CPC .......... A61B 2018/00577; A61B 2018/00714; A61B 2018/00791; A61B 2018/046; A61B 5/0071; A61B 5/0082; A61B 5/01; A61B 5/015; A61F 2007/0054; A61F 2007/009; A61F 7/0053; A61K 41/0052
See application file for complete search history.

(56) References Cited

U.S. PATENT DOCUMENTS

2006/0282140 A1* 12/2006 Schock ...................... A61F 7/00
                                                            607/108
2009/0306646 A1* 12/2009 Turner ................... A61B 18/18
                                                            606/33
2018/0161002 A1* 6/2018 Alford ................. A61B 8/4236

* cited by examiner

*Primary Examiner* — Michael F Peffley
*Assistant Examiner* — Tigist S Demie
(74) *Attorney, Agent, or Firm* — Mintz Levin Cohn Ferris Glovsky and Popeo, P.C.; Andrew Skale, Esq.; F. Jason Far-hadian, Esq.

(57) ABSTRACT

A system and method for hyperthermic ablation of cancerous tissue of a human patient is disclosed. A system and method include a vessel that is sized and adapted for receiving the human patient, and a circulation device outside of the vessel for circulating a thermally conductive liquid to and from the vessel, such that the portion of the human patient enclosed in the containment suit is at least partially submerged in the thermally conductive liquid when the human patient is in the vessel. The system and method further include a set of electromagnetic transmission coils at least partially around the vessel for inducing an alternating electromagnetic field around the human patient, the alternating electromagnetic field being directed, via the thermally conductive liquid, to the cancerous tissue that has been provided a conductive nanoparticle, to provide hyperthermic ablation of the cancerous tissue.

21 Claims, 6 Drawing Sheets

HYPERTHERMIC CANCEROUS TISSUE ABLATION

BACKGROUND

The present invention relates to cancerous tissue ablation, and more particularly to a system and method for a more efficacious treatment of malignant tumors using a process of destroying cancerous tissue with hyperthermic ablation.

Tumor ablation is an image-guided technique to guide a heated needle electrode into a cancerous tumor and use heat to destroy cancer cells. In radio frequency (RF) ablation, imaging techniques such as ultrasound, computed tomography (CT) or magnetic resonance imaging (MRI) are used.

SUMMARY

This document describes a system and method for hyperthermic tumor ablation. More particularly, a system and method is presented for a more efficacious treatment of malignant tumors using the method of destroying cancerous tissue with hyperthermic ablation.

In one aspect, a system for hyperthermic ablation of cancerous tissue of a human patient is disclosed. The cancerous tissue is provided a conductive nanoparticle. The system includes a vessel that is sized and adapted for receiving the human patient, at least one inlet pipe to the vessel, and at least one outlet pipe from the vessel. The system further includes a circulation device outside of the vessel and connected between the at least one inlet pipe and the at least one outlet pipe. The circulation device circulates a thermally conductive liquid to and from the vessel, such that the human patient is at least partially submerged in the thermally conductive liquid when the human patient is in the vessel. The system further includes a set of electromagnetic transmission coils at least partially around the vessel for inducing an alternating electromagnetic field around the human patient, the alternating electromagnetic field being directed to the cancerous tissue that has been provided the conductive nanoparticle via the thermally conductive liquid.

In an alternative aspect, a system can include a flexible containment suit that is sized and adapted for containing at least a portion of the human patient. The containment suit includes a closure system to enclose the containment suit around the portion of the human patient. The containment suit further includes at least one inlet channel and at least one outlet channel for conveying a thermoregulatory fluid to and from the containment suit, respectively.

In yet another aspect, a method of hyperthermic ablation of cancerous tissue of a human patient includes the steps of providing a conductive nanoparticle to or proximate the cancerous tissue, and providing the human patient to a vessel that is sized and adapted for receiving the human patient, the vessel having at least one inlet pipe to the vessel and at least one outlet pipe from the vessel. The method further includes the steps of circulating a thermally conductive liquid to and from the vessel via the inlet pipe and outlet pipe respectively, such that the human patient is at least partially submerged in the thermally conductive liquid when the human patient is provided to the vessel. The method further includes the steps of inducing an alternating electromagnetic field around the human patient via a set of electromagnetic transmission coils at least partially around the vessel, and directing, via the thermally conductive liquid, the alternating electromagnetic field to the cancerous tissue that has been provided the conductive nanoparticle.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This document describes a system and method for hyperthermic tumor ablation. In some implementations, a system and method for hyperthermic ablation of cancerous tissue of a human patient includes providing a conductive nanoparticle to or near the cancerous tissue. A system includes a vessel that is sized and adapted for receiving the human patient, at least one inlet pipe to the vessel, and at least one outlet pipe from the vessel. The system further includes a circulation device outside of the vessel, and which is connected between the at least one inlet pipe and the at least one outlet pipe. In alternative implementations, the circulation device can be located within the vessel, proximate the patient. The circulation device circulates a thermally conductive liquid to and from the vessel, where the liquid is maintained at a predetermined temperature, and also may be maintained at a substantially bio-similar state with respect to salinity, etc. The human patient is at least partially submerged in the thermally conductive liquid when the human patient is in the vessel. The system further includes a set of electromagnetic transmission coils at least partially around the vessel for inducing an alternating electromagnetic field around the human patient. The alternating electromagnetic field is directed to the cancerous tissue, via the thermally conductive liquid, and toward the conductive nanoparticle for ablating the associated cancerous tissue and avoiding ablation of healthy tissue.

Figure 1:
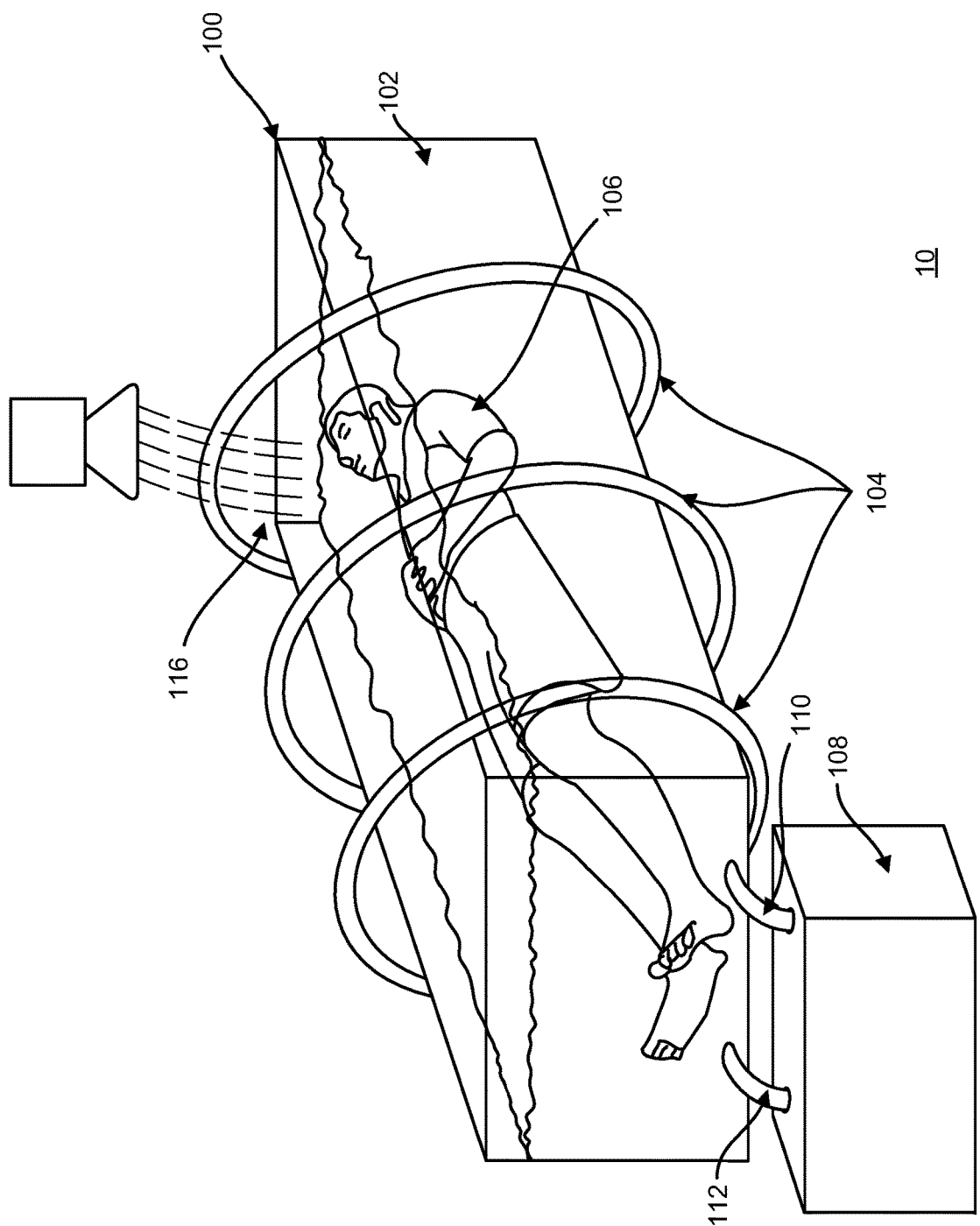
FIG. 1 describes a thermoregulation system for controlling the core body temperature of a human subject undergoing treatment.

FIG. 1 illustrates a thermoregulation system 10 for controlling a core body temperature of a human patient 106 who is undergoing treatment for a cancerous mass. A tank or vessel 100 contains a thermally conductive liquid 102 that transfers thermal energy to or from the patient 106 undergoing treatment. In preferred implementations, the patient 106 is surgically implanted with a ferrous, gold, or conductive nanoparticle, in or proximate to the cancerous mass.

The thermoregulation system 10 includes electromagnetic transmission antennas or coils 104 that induce an alternating electromagnetic field that is absorbed to a lesser degree by human tissues, and in particular to a greater degree by the cancerous tumor tissue that has taken up, or is proximate to, the surgically implanted ferrous, gold, or conductive nanoparticle. The electromagnetic transmission coils 104 may further include conductive tubing through which a coolant can be circulated to prevent overheating of the coils 104.

The thermally conductive liquid 102 may be circulated in the tank or vessel 100 to aid in the thermal transfer of energy from the patient or person undergoing treatment 106. The circulated thermally conductive liquid 102 may come from inlet pipes 112, pass through an exchange unit 108, such as, for example, a pump and/or refrigeration and/or heating control unit, and then be circulated in close proximity to the patient through outlet pipes 110. There may be one or more of each inlet and outlet pipes located in more than one place in the tank or vessel 100 to facilitate the greatest equilibrium of temperature between the patient 106 and the thermally conductive liquid 102.

In some implementations, the thermally conductive liquid 102 may be electrically conductive to absorb the electromagnetic voltage gradient induced by the electromagnetic transmission antennas or coils 106 so as to reduce or prevent surface heating of the skin of the patient undergoing treatment 106. In some other implementations, the liquid 102 may be completely non-conductive. The liquid 102 may alternatively be formulated to have a very similar composition of sodium and/or other ions to be very similar to the electrical conductivity of bodily liquids such as blood. Examples of some liquids that could be used include, without limitation, deionized water, water with an isotonic solution of sodium ions, and various oils.

In some implementations, the patient 106 may be in direct contact with the liquid, however in other implementations, a flexible membrane can be used around the patient 106 to separate the patient 106 from direct contact with the liquid 102.

The system 10 can further include a thermal imaging device 114, such as a thermal imaging camera or imaging pyrometer (H), to measure the temperature of one or more locations of the liquid 102 and/or patient 106, and to determine if the temperature of the liquid 102 and/or patient 106 at those locations is within safe and effective operating parameters. If no thermally conductive liquid 102 is used, the thermal imaging device 114 may be used to measure large portions, or the entire body, of the patient 106 undergoing treatment to determine whether the temperature of the patient 106 is within safe and/or effective operating parameters. Alternatively, one or more other biometric sensors 116, such as a contact thermometer, may be used to measure a body orifice temperature of the patient 106. One or more such biometric sensors 116 may be may be placed to measure a number of vital body signs, such as, for example, temperature, heart-rate and electrocardiogram (EKG), respiration, pulse oximetry, capnography, or the like, or allow sampling of bodily fluids or to introduce drugs to the patient.

Figure 2:
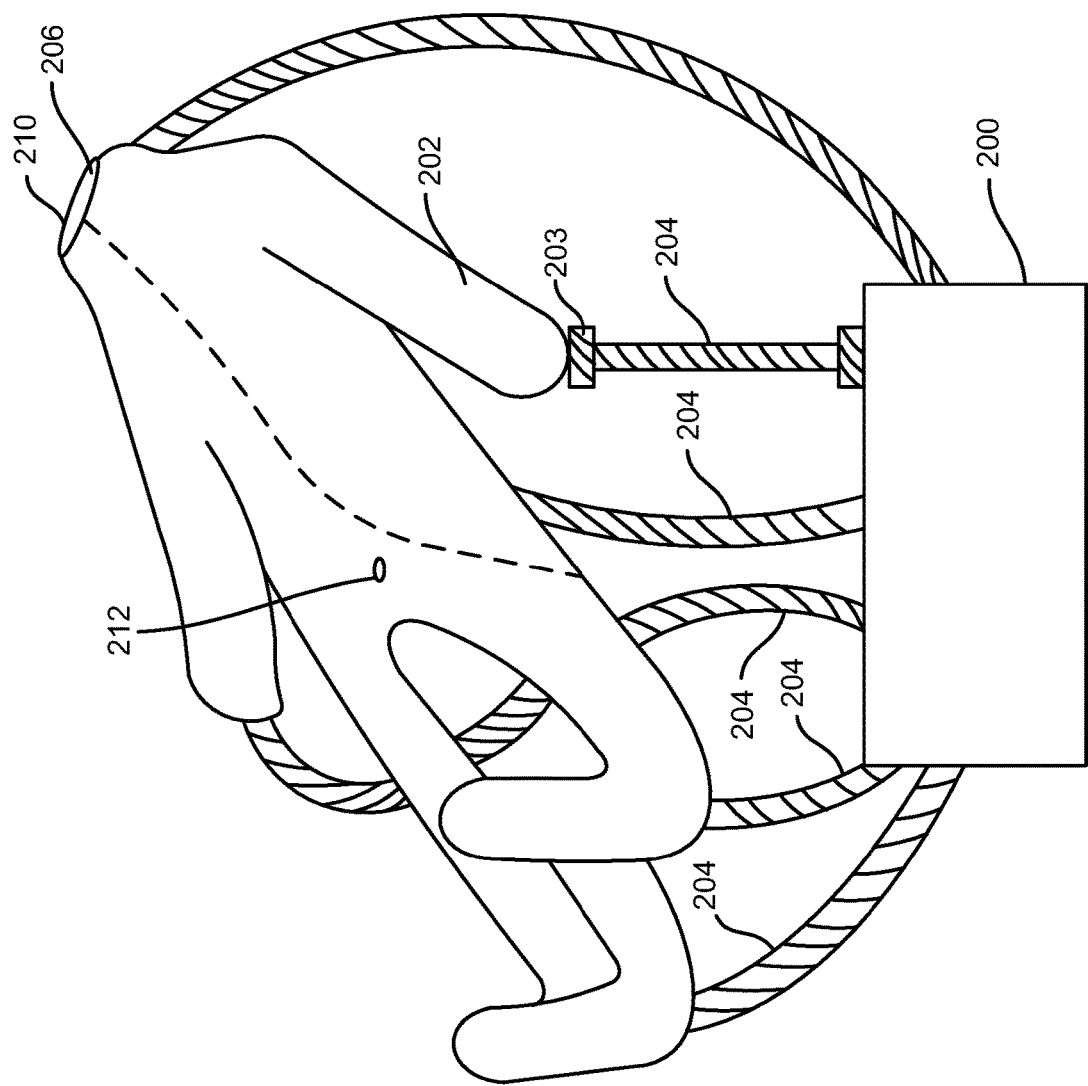
FIG. 2 illustrates a containment suit for thermoregulatory liquid or gasses.

FIG. 2 illustrates a containment system 20 for containing thermoregulatory liquids or gasses. The containment system 20 includes containment suit 202 that is sized and adapted to accommodate a human patient 208 undergoing hyperthermic ablation treatment. The containment suit 202 can be configured to either include or exclude a thermally conductive liquid from direct contact with the patient 208. The containment suit 202 may have a closure system 210 that allows the patient 208 to be introduced and to be at least partially, and preferably mostly, contained within the containment suit 202. The closure system 210 can include one or more closure devices 206, such as, for example, an elastic band, a zipper system, adhesives or hook-and-fabric closure systems such as Velcro®. The containment suit 202 may also have a gland or a gasket to facilitate sealing of containment suit 202 against the body of a patient 208 to prevent ingress or egress of thermally conductive gasses or liquids. The closure system 210 and associated closure devices 206 can be located or positioned at extremities of the body such as the face, nose, mouth, neck, hands, feet, arms, or legs.

The containment system 20 includes a number of pipes or channels 204 to transfer the thermally conductive liquid or gas to a thermal exchange unit 200 to regulate the temperature of the patient undergoing treatment. Couplers 203 connect the pipes or channels 204 to the containment suit 202 and the thermal exchange unit 200. One or more biometric sensors 212, or ports therefor, may be placed within the containment suit 202 to measure vital body signs which can include temperature, heart-rate and EKG, respiration, pulse oximetry, capnography, or allow sampling of body-fluids or to introduce drugs to the patient.

Figure 3:
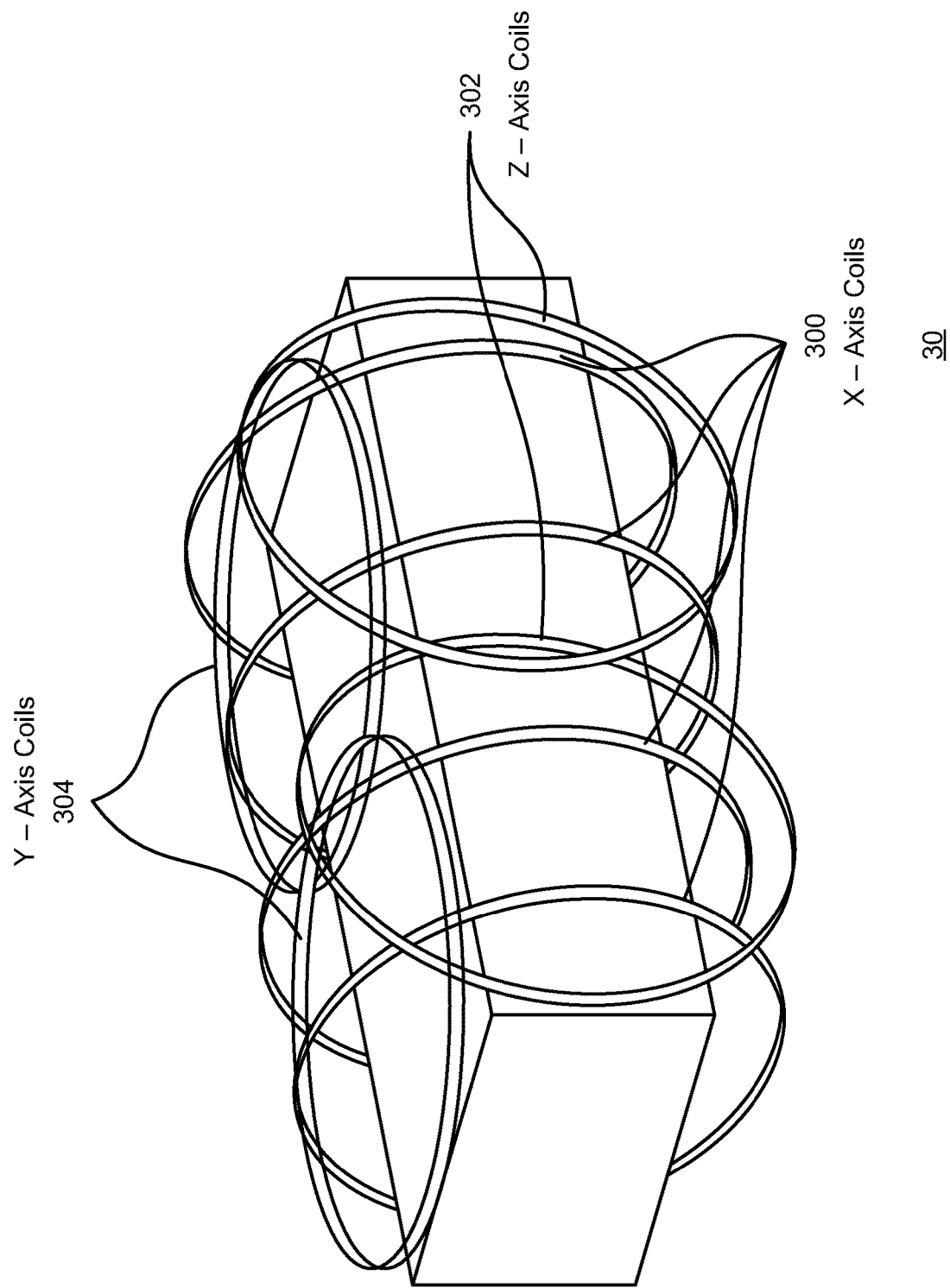
FIG. 3 illustrates electromagnetic coil configurations.

FIG. 3 illustrates an electromagnetic coil configuration 30. The coil configuration 30 includes a number of coils, 300, 302, and 304, that can be configured in one or more axes, such as (X, Y, Z), respectively, to optimally focus electromagnetic energy towards the cancerous tissues within the patient being treated. The configuration 30 may be single coil, a Helmholtz configuration, or in a spacing that allows for an interference pattern to optimally focus the electromagnetic energy towards the cancerous tissue to be treated. The configuration 30 may also be in a phased array that allows for focusing of the electromagnetic radiation in specific patterns. The configuration 30 can further include a steering mechanism to "steer" a pattern of electromagnetic radiation emanating from the coils 300, 302 and 304 to an optimally focused pattern.

Figure 4:
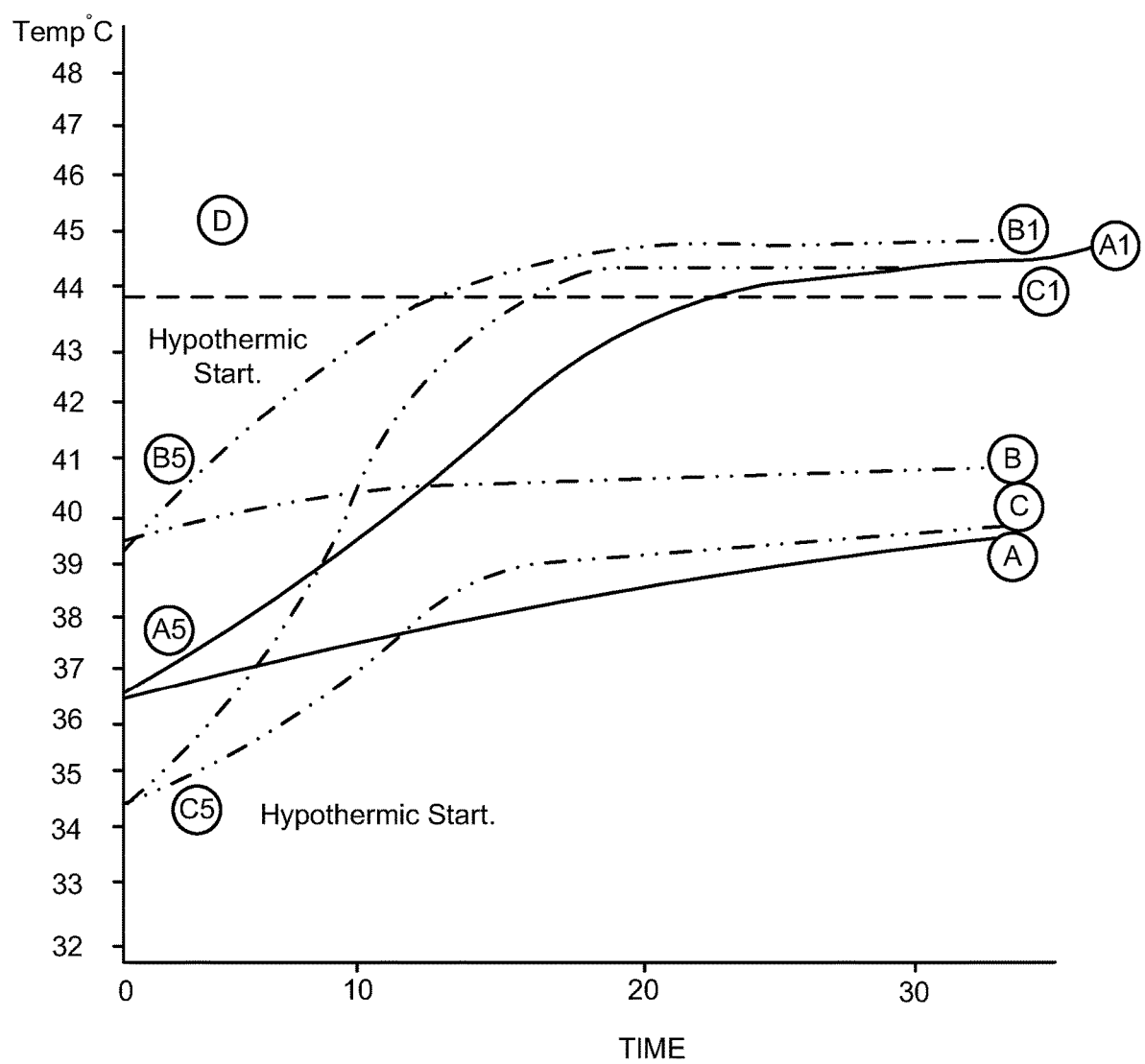
FIG. 4 illustrates manipulation of the patient systemic temperature.

FIG. 4 illustrates manipulation of the patient's systemic temperature. The thermoregulatory system of the patient or the core body temperature of the patient may be manipulated to induce a systemic hyperthermic or hypothermic state to facilitate a more effective and/or safe elevation of the cancerous tumor tissue into a temperature that would cause apoptosis of the cancerous cells while minimizing harm to the healthy body tissue of the patient.

In FIG. 4, a graph shows a temperature on the Y axis, and a time of treatment on the X axis. The graph shows three possible starting conditions, as examples, and other temperatures and curves of temperature change may be used:

Condition AS, where the system body temperature is at a normative temperature of 37 degrees Celsius, and the cancerous tissue is at the same temperature. Over time, when exposed to energy introduced by electromagnetic or laser radiation, the temperature of both the healthy tissue (A) and cancerous tissue (A1) will increase. The goal is to increase the temperature of the cancerous tissue (A1) above a thermal threshold (D–44.5 C) whereat the cancerous tissue will die, while preserving the temperature of the healthy tissue to a level that is safe (A).

Condition BS, where the system body temperature is at a hyperthermic temperature of 39.5 C, and the cancerous tissue is at the same temperature. Over time, when exposed to energy introduced by electromagnetic or laser radiation, the temperature of both the health tissue (A) and cancerous tissue (A1) will increase. The goal is to increase the temperature of the cancerous tissue (A1) above a thermal threshold (D) at where the cancerous tissue will die, while preserving the temperature of the healthy tissue to a level that is safe (A). In this case, a lower delta between the systemic temperature and healthy tissue and that of the cancerous tissue is required, which may speed and increase the efficacy of the treatment. This may also increase the destruction of tissue at the boundary of the cancerous tissue and healthy tissue so as to ensure destruction of an extra margin of tissue to prevent survival of cancerous cells at the edge of the tumor.

Condition CS, where the system body temperature is at a hypothermic temperature of 35 C, and the cancerous tissue is at the same temperature. Over time, when exposed to energy introduced by electromagnetic or laser radiation, the temperature of both the health tissue (A) and cancerous tissue (A1) will increase. The goal is to increase the temperature of the cancerous tissue (A1) above a thermal threshold (D) at where the cancerous tissue will die, while preserving the temperature of the healthy tissue to a level that is safe (A). In this case, a higher delta between the systemic temperature and healthy tissue and that of the cancerous tissue is required, which may allow for higher amounts of power to be introduced into the cancerous tissue which may either increase the efficacy of the treatment or minimize the damage to the tissue that is at the boundary of the cancerous tissue and healthy tissue.

Systemic drugs that affect the thermoregulation of the body may be introduced to the patient to assist in the manipulation of the patient's systemic temperature. Examples of such systemic drugs are anti-pyretic drugs such as aspirin or acetaminophen. It also may be necessary to sedate or immobilize the patient during treatment. Additional or alternative core temperature manipulation techniques could include rectal or esophageal irrigation with a thermally conductive liquid, or extracorporeal circulatory manipulation of blood temperature.

Figure 5:
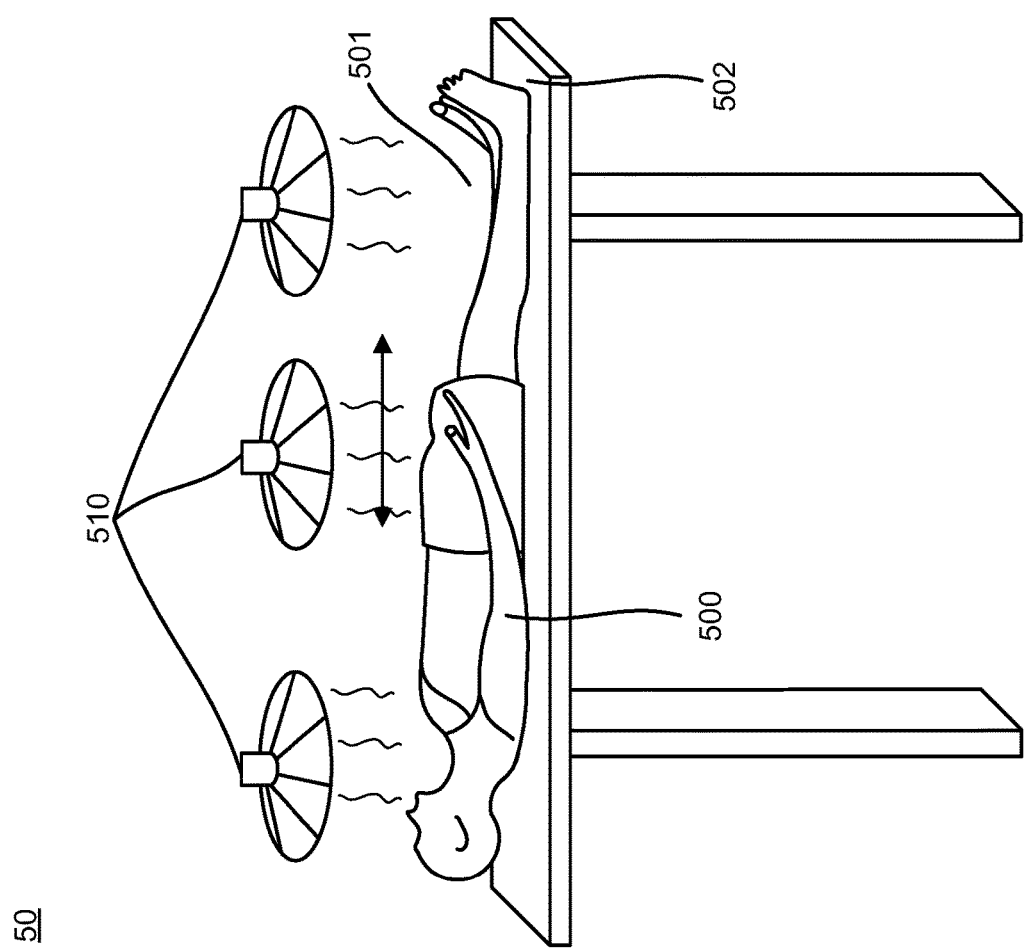
FIG. 5 illustrates a gantry system and thermal monitoring and regulation thereby.
Figure 5:
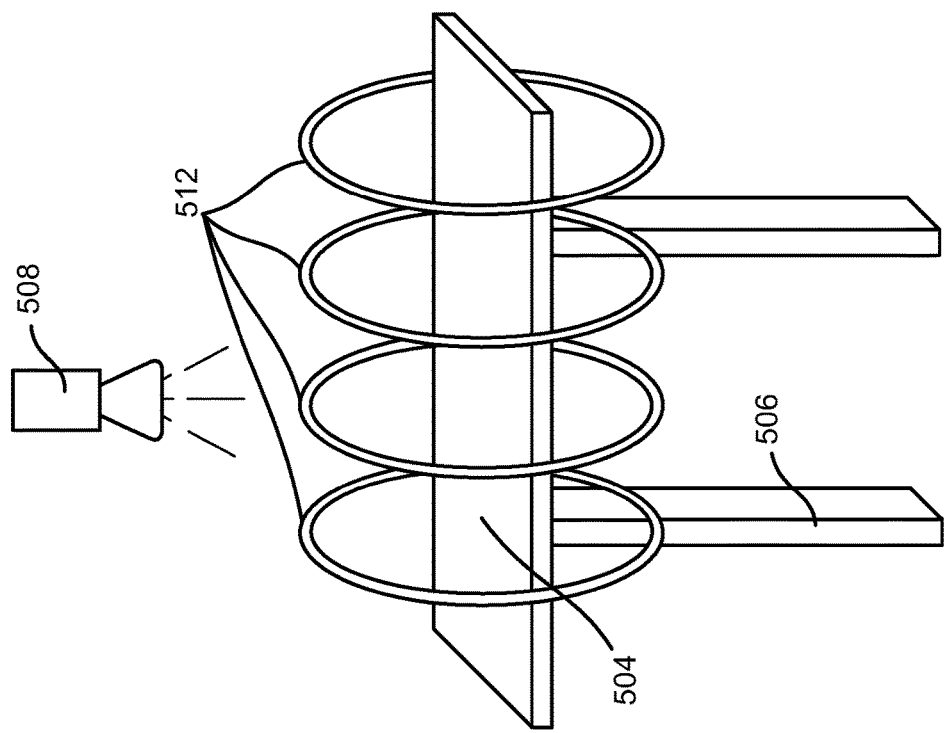

FIG. 5 shows a system 50 that facilitates introduction of the patient to a location within the electromagnetic transmission system, as well as placement thermal imaging pyrometers and cameras. In some preferred exemplary implementations, the patient 502 is placed on a moveable gurney 500. The gurney is preferably made of non-conductive materials. The gurney 500 is able to move along a single axis 501 in a direction axial to electromagnetic transmission coils 512. An elevation device 506 positions and suspends the gurney 500 and/or coils 512 at a height that facilitates loading of the patient, coil placement, and monitoring and treatment of the patient by staff. Thermal imaging devices 508, such as cameras or pyrometers, allow regular monitoring of the temperature of the patient to ensure that the systemic temperature of the patient is within safe and effective operating parameters.

Air may be circulated over the patient 502 by circulation devices 510, such as fans or vents, to assist in the regulation of the patient systemic temperature to a level that is safe and effective. The circulation devices 510 may be placed at any location under, above, or beside the patient to maintain optimal airflow and thus, maintain the optimal temperature.

Figure 6:
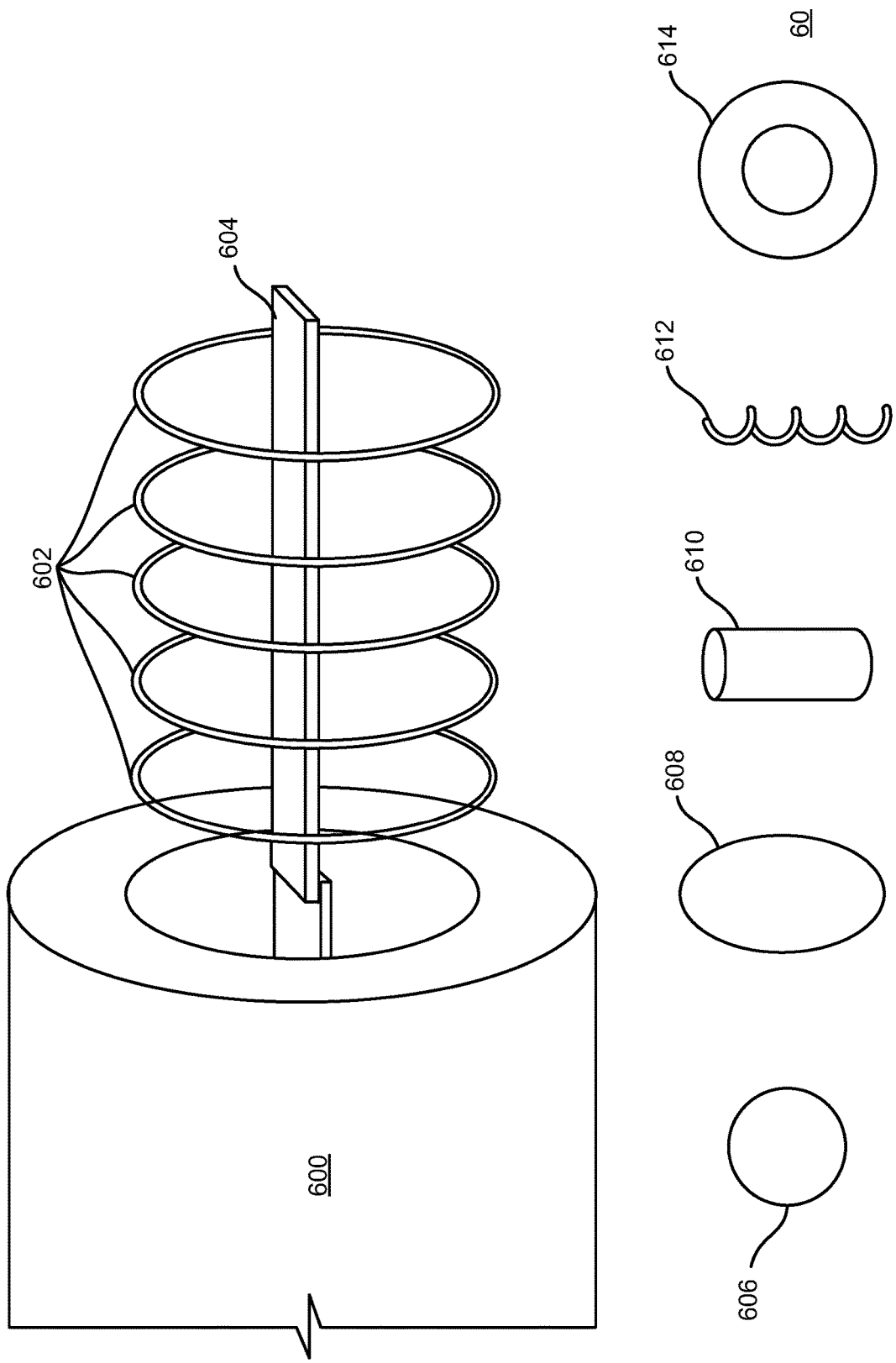
FIG. 6 illustrates manipulation of an electromagnetic field within a strong static magnetic field.

FIG. 6 shows a large superconducting solenoid 60 having a solenoid 600, such as may exist in an MRI machine, and a moveable gurney 604 that may be placed axially within the superconducting solenoid. Electromagnetic field induction coils 602 may be placed axially within the superconducting solenoid near the gurney 604.

The activation of the electromagnetic coils 602 with capacitively discharged pulses of high energy will induce eddy currents and associated magnetic fields in conductive materials such as ferrous or gold nanoparticles, and which will cause the nanoparticles to move or rotate against the large static magnetic field of the superconducting solenoid 600. This physical movement of the nanoparticles within cancerous cells may increase the damage to and destruction of cancerous cells. The nano-particles may be optimally shaped in a non-spherical shape to increase the magnitude of the magnetic field at the poles of each nanoparticle. Examples of shapes that may be superior to spherical nanoparticles 606 for this purpose are ovoid 608, cylindrical 610, helical 612, or toroidal 614.

Although a few embodiments have been described in detail above, other modifications are possible. Other embodiments may be within the scope of the following claims.

The invention claimed is:

1. A system for hyperthermic ablation of cancerous tissue of a human patient, the cancerous tissue being contacted with a plurality of conductive nanoparticles, the system comprising:
    a thermoregulation vessel being defined by a plurality of opposed bounding members that are spaced apart from one another so as to form a cavity there between, the cavity being sized and adapted for receiving an entirety of the human patient;
    at least one inlet pipe, coupled to at least one of the plurality of opposed bounding members of the thermoregulation vessel, the inlet pipe being configured for delivering a thermally conductive liquid to the cavity of the vessel;
    at least one outlet pipe, coupled to at least one of the plurality of opposed bounding members of the thermoregulation vessel, the outlet pipe being configured for conveying the thermally conductive liquid from the cavity of the vessel;
    a circulation device outside of the vessel and associated with the at least one inlet pipe and the at least one outlet pipe, the circulation device for circulating the thermally conductive liquid to and from the vessel, such that the human patient is at least partially submerged in the thermally conductive liquid in a manner such that the conductive liquid at least partially covers the cancerous tissue at a treatment site containing the conductive nanoparticles when the human patient is in the vessel; and
    a plurality of electromagnetic transmission coils positioned to circumscribe the vessel, the plurality of electromagnetic transmission coils being configured for inducing an electromagnetic field around the human patient, the electromagnetic field being directed to the conductive nanoparticles at the treatment site of the cancerous tissue, via the thermally conductive liquid, so as to heat the conductive nanoparticles and thereby cause the ablation of the cancerous tissue.

2. The system in accordance with claim 1, wherein the circulation device includes a pump for circulating the thermally conductive liquid to and from the vessel.

3. The system in accordance with claim 1, further comprising a heating control and exchange unit associated with the circulation device, the heating control and exchange unit for maintaining a temperature of the thermally conductive liquid at predetermined temperature.

4. The system in accordance with claim 3, wherein the predetermined temperature is equal to a core body temperature of the human patient.

5. The system in accordance with claim 1, further comprising one or more biometric sensors proximate the vessel, the one or more biometric sensors for sensing and recording one or more vital body signs for controlling the circulation device.

6. The system in accordance with claim 1, further comprising one or more thermal imaging devices proximate the vessel, the one or more thermal imaging devices for sensing and recording a body temperature of a region of the human patient.

7. The system in accordance with claim 6, wherein the one or more thermal imaging devices includes a thermal imaging camera directed at the region of the human patient.

8. A system for hyperthermic ablation of cancerous tissue of a human patient, the cancerous tissue being treated at least in part by being contacted with a plurality of conductive nanoparticles, the system comprising:
- a rigid thermoregulation vessel being defined by a plurality of opposed bounding members that are spaced apart from one another so as to form a cavity there between, the cavity being sized and adapted for receiving an entirety of the human patient;
- a flexible containment suit having an interior portion that is sized and adapted for containing at least a portion of the human patient having the cancerous tissue at a treatment site defined by the plurality of conductive nanoparticles, the containment suit having a closure system to enclose the containment suit around the portion of the human patient, the containment suit further having at least one inlet channel and at least one outlet channel for conveying a thermoregulatory fluid to and from the interior portion of the containment suit respectively;
- at least one inlet pipe, coupled to at least one of the plurality of opposed bounding members of the rigid thermoregulation vessel, the inlet pipe being configured for delivering a thermally conductive liquid to the interior portion of the containment suit via the inlet channel;
- at least one outlet pipe, coupled to at least one of the plurality of opposed bounding members of the thermoregulation vessel, the outlet pipe being configured for conveying the thermally conductive liquid from the interior portion of the containment suit via the outlet channel;
- a circulation device outside of the vessel associated with the at least one inlet pipe and the at least one outlet pipe, the circulation device for circulating the thermally conductive liquid to and from the interior portion of the containment suit, such that the portion of the human patient enclosed in the containment suit is at least partially contacted by the thermally conductive liquid in a manner so that the thermally conductive liquid at least partially covers the treatment site when the human patient is in the vessel; and
- a plurality of electromagnetic transmission coils positioned to circumscribe the vessel, the plurality of electromagnetic transmission coils being configured for inducing an electromagnetic field around the human patient, the electromagnetic field being directed to the conductive nanoparticles at the treatment site of the cancerous tissue, via the thermally conductive liquid, so as to heat the conductive nanoparticles and thereby cause the ablation of the cancerous tissue.

9. The system in accordance with claim 8, wherein the circulation device includes a pump for circulating the thermally conductive liquid to and from the interior portion of the containment suit.

10. The system in accordance with claim 8, further comprising a heating control and exchange unit associated with the circulation device, the heating control and exchange unit for maintaining a temperature of the thermally conductive liquid at predetermined temperature.

11. The system in accordance with claim 10, wherein the predetermined temperature is equal to a core body temperature of the human patient.

12. The system in accordance with claim 8, further comprising one or more biometric sensors proximate the cancerous tissue of the human patient, the one or more biometric sensors for sensing and recording one or more vital body signs for controlling the circulation device.

13. The system in accordance with claim 8, further comprising one or more thermal imaging devices proximate the vessel, the one or more thermal imaging devices for sensing and recording a body temperature of a region of the human patient.

14. The system in accordance with claim 13, wherein the one or more thermal imaging devices includes a thermal imaging camera directed at the region of the human patient.

15. A method of hyperthermic ablation of cancerous tissue of a human patient, the method comprising:
- contacting the cancerous tissue of the human patient with a plurality of conductive nanoparticle so as to define a treatment site;
- inserting at least a portion of the human patient including the treatment site into a thermoregulation vessel, the thermoregulation vessel being defined by a plurality of opposed bounding members that are spaced apart from one another so as to form a cavity there between, the cavity being sized and adapted for receiving an entirety of the human patient, the vessel having:
  - at least one inlet pipe coupled to at least one of the plurality of opposed bounding members of the thermoregulation vessel, the inlet pipe being configured for delivering a thermally conductive liquid to the cavity of the vessel;
  - at least one outlet pipe coupled to at least one of the plurality of opposed bounding members of the thermoregulation vessel, the outlet pipe being configured for conveying the thermally conductive liquid from the cavity of the vessel;
  - a circulation device outside of the vessel and associated with the at least one inlet pipe and the at least one outlet pipe, the circulation device for circulating the thermally conductive liquid to and from the vessel in a manner such that the conductive liquid at least partially covers the cancerous tissue at the treatment site defined by the conductive nanoparticles; and
  - a plurality of electromagnetic transmission coils positioned to circumscribe the vessel, the plurality of electromagnetic transmission coils being configured for inducing an electromagnetic field around the portion of the human patient inserted into the thermoregulation vessel;
- engaging the circulation device for circulating the thermally conductive liquid to and from the vessel via the inlet pipe and outlet pipe respectively, such that the portion of the human patient inserted into the thermoregulation vessel is at least partially submerged in the thermally conductive liquid in a manner such that the thermally conductive liquid contacts the treatment site proximate the conductive nanoparticles;
- activating the electromagnetic transmission coils for inducing an electromagnetic field around the cancerous tissue of the human patient via the plurality of electromagnetic transmission coils; and
- directing the electromagnetic field to the conductive nanoparticles at the treatment site, via the thermally conductive liquid, so as to heat the conductive nanoparticles and thereby cause the ablation of the cancerous tissue.

16. The method in accordance with claim 15, further comprising maintaining, via a heating control and exchange unit, a temperature of the thermally conductive liquid at predetermined temperature.

17. The method in accordance with claim 16, wherein the predetermined temperature is equal to a core body temperature of the human patient.

18. The method in accordance with claim 15, further comprising sensing and recording, by one or more biometric sensors proximate the human patient, one or more vital body signs, the sensing and recording providing feedback for controlling the circulating of the thermally conductive liquid.

19. The method in accordance with claim 15, further comprising sensing and recording, via one or more thermal imaging devices proximate the vessel, a body temperature of a region of the human patient.

20. The method in accordance with claim 15, further comprising providing a containment suit, and inserting the portion of the human patient containing the treatment site into the containment suit prior to insertion into the thermoregulation vessel, the containment suit being configured to enclose and seal around the treatment site.

21. A system comprising:
- a vessel sized and adapted for receiving an entirety of a human patient;
- at least one inlet pipe to the vessel, the inlet pipe being configured for delivering a thermally conductive liquid to the vessel;
- at least one outlet pipe from the vessel;
- a circulation device outside of the vessel and associated with the at least one inlet pipe and the at least one outlet pipe, the circulation device for circulating the thermally conductive liquid to and from the vessel, such that the human patient is at least partially submerged in the thermally conductive liquid at a treatment site when the human patient is in the vessel; and
- one or more electromagnetic transmission coils positioned to at least partially circumscribe the vessel for inducing an electromagnetic field around the human patient, the electromagnetic field being directed to the treatment site.

* * * * *